United States Patent [19]

Widmer

[11] 4,005,145

[45] Jan. 25, 1977

[54] PROCESS FOR THE MANUFACTURING OF OXO COMPOUNDS

[75] Inventor: Erich Widmer, Munchenstein, Switzerland

[73] Assignee: Hoffmann-La Roche Inc., Nutley, N.J.

[22] Filed: Feb. 21, 1975

[21] Appl. No.: 551,945

[30] Foreign Application Priority Data

Mar. 1, 1974 Switzerland ...................... 2933/74
Jan. 30, 1975 Switzerland ...................... 1124/75

[52] U.S. Cl. ...................... 260/586 R; 260/593 R; 260/598; 260/601 R

[51] Int. Cl.² ........................................ C07C 45/00

[58] Field of Search ....... 260/586 R, 593 R, 593 P, 260/601 R, 598

[56] References Cited

UNITED STATES PATENTS

| | | | |
|---|---|---|---|
| 2,968,677 | 1/1961 | Fewlass | 260/586 R |
| 3,397,120 | 8/1968 | Diana et al. | 260/586 R |
| 3,538,164 | 11/1970 | Leffingwell | 260/586 R |
| 3,770,829 | 11/1973 | Wellman et al. | 260/586 R |
| 3,962,348 | 8/1969 | Wellman et al. | 260/586 R |

OTHER PUBLICATIONS

Weygand, "Prep. Org. Chem.," 4th Ed., p. 1056 (1972).
Stross et al., "J.A.C.S.," vol. 69, pp. 1627–1628 (1947).
Hess et al., "Chem. Ber.," vol. 100, pp. 923–929 (1967).

*Primary Examiner*—Norman Morgenstern
*Attorney, Agent, or Firm*—Samuel L. Welt; Bernard S. Leon; William H. Epstein

[57] ABSTRACT

A process for isomerizing α, β-unsaturated oxo compounds to the corresponding β, γ-unsaturated oxo compound utilizing a weak acid as catalyst.

15 Claims, No Drawings

PROCESS FOR THE MANUFACTURING OF OXO COMPOUNDS

BACKGROUND OF THE INVENTION

There have already been many attempts to isomerize α,β-unsaturated oxo compounds with the aid of bases or acids in order to produce the corresponding β,γ-unsaturated oxo compounds. For example, in U.S. Pat. No. 2,197,462 4-methyl-nona-4-en-6-one has been isomerized in the presence of sodium ethylate in moderate yields to give 4-methyl-nona-3-en-6-one and in U.S. Pat. No. 3,385,903 isophorone has been isomerized with the aid of p-toluenesulfonic acid to give in part β-isophorone. A more precise examination of this latter reaction has demonstrated that with the use of p-toluenesulfonic acid as the catalyst, there is always obtained at best a mixture of equal parts of isophorone and β-isophorone in which the β-isophorone is unstable and is converted at least partly back into isophorone.

SUMMARY OF THE INVENTION

Although the acid-catalyzed isomerization seems unproductive and of little promise, it has now surprisingly been found in accordance with the present invention that α,β-unsaturated oxo compounds can be isomerized in very good yields to give the corresponding β,γ-unsaturated oxo compounds when there are used as catalysts acids which are stable under the reaction conditions and which have a pK value of from about 2 to 5 and a boiling point above that of the isomerization products.

DETAILED DESCRIPTION

The term "α,β-unsaturation" designates an unsaturated olefinic double bond between the carbon atoms which are alpha and beta to the carbon atom containing the oxo substituent. The term "β,γ-unsaturation" designates an unsaturated olefinic double bond between the carbon atoms which are beta and gamma to the carbon atom containing the oxo substituent.

The term "acids which are stable under the reaction conditions" denotes acids which are inert, under the reaction conditions, i.e., they are neither transformed at the isomerization temperature nor do they enter into any sort of side reactions with the starting materials or end products. The pK range of from about 2 to 5 denotes the degree of dissociation in water of the acids utilized in the process of this invention. This pK range as given denotes that the dissociation constant is measured under standard conditions, i.e., room temperature and atmospheric pressure.

The boiling point of the acid used should be appreciably higher, e.g., from 20° C. to 200° C. higher, than the boiling point of the isomerization product to prevent acid fractions coming over during the rectification and contaminating the distilled material. Acids which fulfill the above criteria are especially suitable as catalysts for continuous isomerization processes since, because of their stability they can be used over a long period without having to be supplemented or exchanged. Further, since these acids are less volatile than the isomerization products, the distillates which in practice are isomerized back to the starting materials in the presence of even slight amounts of acids or acidic decomposition products, remain acid-free and accordingly stable.

The present invention is based on the foregoing findings and is accordingly concerned with a process for the manufacture of β,-unsaturated oxo compounds by acid-catalyzed isomerization of the corresponding α,β-unsaturated oxo compounds, wherein as the isomerization catalyst there is used an acid which is stable under the reaction conditions, which has a pK value of from about 2 to about 5 and a boiling point above that of the isomerization product. The β,γ-unsaturated oxo compound is recovered from the reaction mixture in which it was formed by distillation.

In accordance with the present invention, the process can be applied to isomerizing any α,β-unsaturated oxo compound to the corresponding β,γ-unsaturated oxo compound. The acids described above can be utilized to isomerize any ketone or aldehyde of a hydrocarbon which has an α,β-olefinic unsaturation and which is saturated at the β,γ-position. The product of isomerization is the corresponding β,γ-unsaturated aldehyde or ketone. Where a ketone of a hydrocarbon is utilized which has two α,β-unsaturated olefinic bonds, both α,β-unsaturated bonds can be converted to β,γ-olefinic unsaturated bonds. Furthermore, the isomerization does not affect any other double bonds which may be present at other positions in the hydrocarbon moiety of the aldehyde or ketone.

Among the preferred isomerizable α,β-unsaturated oxo compounds which can be utilized in the process of this invention are the cyclic and open-chain oxo compounds such as:
   isophorone (3,5,5-trimethyl-2-cyclohexen-1-one);
   carvone;
   cyclohex-2-en-1-one;
   mesityl oxide;
   phorone;
   citral; and
   pent-3-en-2-one.

Any acid which has a pK of from 2 to 5, which is stable under the reaction conditions and which has a boiling point higher than the product produced can be utilized in the process of this invention.

Examples of some of the acids which may be used as the isomerization catalysts are:
   a. monocyclic, aromatic or alicyclic monocarboxylic, dicarboxylic or polycarboxylic acids which may contain a hetero atom and/or be ring-substituted, such as:
      p-toluic acid;
      4-nitro-m-toluic acid;
      4-hydroxybenzoic acid;
      3-hydroxy-4-nitrobenzoic acid;
      4-trifluoromethylbenzoic acid;
      vanillic acid;
      3,4,5-trimethoxybenzoic acid;
      5-nitroisophthalic acid;
      chelidamic acid; and
      cyclohexanecarboxylic acid;
   b. saturated or unsaturated, aliphatic or heteroaliphatic monocarboxylic, dicarboxylic or polycarboxylic acids which may be hydroxylated and/or phenyl-substituted, such as:
      adipic acid;
      12-hydroxystearic acid;
      benzilic acid;
      and
      diglycolic acid;
   c. aliphatic or aromatic amino acids such as:
      indolebutryic acid; and 1,2-diamino-cyclohexanetetraacetic acid;
d. inorganic acids, such as: metaphosphoric acid; and phenylphosphinic acid.

The said acids which are used as isomerization catalysts are employed according to the acid strength in a concentration of about 0.1 to about 20 mole percent based upon the moles of α,β-unsaturated oxo compounds employed as the starting material, preferably in an amount of about 4 to 10 mole percent.

In carrying out the isomerization of this invention, the α,β-unsaturated alcohol and acid catalyst are heated to reflux. Any combination of temperature and pressure which is sufficient to reflux the reaction mixture can be utilized in accordance with this invention. In accordance with this invention, isomerization occurs at reflux. This reaction is preferably carried out without the necessity of utilizing an inert solvent medium. In general, the oxo compound will act as the solvent medium. If desired, however, inert organic solvents can be utilized in the reaction medium. The reaction is carried out under conditions sufficient to distill the β,γ-unsaturated oxo compound.

As mentioned initially, because of their stability and low vapor pressure, the isomerization catalysts employed in the process of the present invention are especially suitable for continuous isomerization processes. Thus, they are preferably used in a continuous isomerization process in which the α,β-unsaturated oxo compound is continuously fed into the reaction vessel in an amount equal to that of the distillate being continuously removed from the reaction vessel via the distillation column. The isomerization product is separated from the residual starting material by rectification. The type and size of the column used [plate or packed column], the isomerization temperatures and the duration of the isomerization are all conventional in the art. The preferred types and sizes of the columns used [plate or packed column], the isomerization temperatures and the duration of isomerization are all dependent on the substance mixtures employed in each case. The isomerization process of the present invention may be carried out at temperatures lowered by means of a reduced pressure. Normally, however, the process is carried out at atmospheric pressure.

The following Examples illustrate the present invention. In the Examples, isophorone is 3,5,5-trimethyl-2-cyclohexen-1-one and β-isophorone is 3,5,5-trimethyl-3-cyclohexen-1-one.

EXAMPLE 1

After the addition of 38 g. of adipic acid to 553 g. of isophorone, the mixture is heated to boiling at atmospheric pressure. The β-isophorone C formed is distilled off via a rectification attachment. The reflux is controlled such that 11 ml. of β-isophorone/isophorone mixture distill over per hour. The distillate collected after 50 hours (456 g.) consists of 91% β-isophorone and 9% isophorone. The β-isophorone is separated from the isophorone by repeated rectification at 68°–69° C/11 mm Hg. There are obtained 412 g. of pure β-isophorone and 42 g. of isophorone. The conversion of isophorone to β-isophorone comes to 428 g.

The yield of β-isophorone is 74.5% with respect to the amount of isophorone employed or 96.3% with respect to the amount of isophorone reacted.

The catalyst employed in the foregoing can readily be used in subsequent isomerization batches.

Under the foregoing conditions and in a continuous manner, starting from an initial 5530 g. of isophorone (5390 g. of isophorone are converted) there is obtained a total of 5241 g. of β-isophorone. The yield of β-isophorone with respect to the initial amount of isophorone comes to 94.8% and with respect to the converted isophorone to 97.2%.

EXAMPLE 2

By the procedure of Example 1, isophorone with the aid of the acids listed in the following Table is converted to β-isophorone. In the Table, the obtained distillates, with β-isophorone contents are listed adjacent to each of said acids:

Table

| Acid | β-Isophorone content |
|---|---|
| 4-Nitro-m-toluic acid | 94% |
| 4-Hydroxybenzoic acid | 83% |
| 3-Hydroxy-4-nitrobenzoic acid | 89% |
| 4-Trifluoromethylbenzoic acid | 93% |
| Vanillic acid | 83% |
| 3,4,5-Trimethoxybenzoic acid | 90% |
| 5-Nitroisophthalic acid | 92% |
| Chelidamic acid | 85% |
| Cyclohexanecarboxylic acid | 76% |
| Adipic acid | 91% |
| 12-Hydroxystearic acid | 72% |
| Benzilic acid | 77% |
| Diglycolic acid | 75% |
| 1,2-Diamino-cyclohexanetetraacetic acid | 87% |
| Indolebutyric acid | 90% |
| Metaphosphoric acid | 80% |
| Phenylphosphinic acid | 96% |

EXAMPLE 3

The following isomerisation reactions can be carried out in a manner analogous to that described in Example 1:

Isomerisation of mesityl oxide to β-mesityl oxide by means of adipic acid;

isomerisation of pent-3-en-2-one to pent-4-en-2-one (β-pentenone) by means of adipic acid, isomerisation of phorone to β-phorone by means of adipic acid;

isomerisation of citral to β-citral (cis/trans mixture) and iso-β-citral by means of phenylphosphonic acid;

isomerisation of cyclohex-2-en-1-one to cyclohex-3-en-1-one by means of adipic acid;

isomerisation of carvone to β-carvone by means of adipic acid.

I claim:

1. A process for isomerizing an α,β-unsaturated oxo compound to a β,γ-unsaturated oxo compound comprising boiling an α,β-unsaturated oxo compound in the presence of a catalyst, said catalyst being an acid having a pK value at room temperature and atmospheric pressure of from 2 to 5, a boiling point of greater than that of said β,γ-unsaturated oxo compound and which is stable under the reaction conditions, said catalyst being selected from the group consisting of
   a. monocyclic, aromatic or alicyclic monocarboxylic, dicarboxylic or polycarboxylic acids which may contain a hetero atom and/or be ring-substituted;
   b. an acid selected from the group consisting of adipic acid, 12-hydroxystearic acid, benzilic acid and diglycolic acid; and
   c. aliphatic or aromatic amino acids;

to form said β,γ-unsaturated oxo compound which is collected in the distillate.

2. The process of claim 1 wherein said α,β-unsaturated oxo compound is a cyclic α,β-unsaturated oxo compound.

3. The process of claim 2 wherein said α,β-unsaturated oxo compound is isophorone.

4. The process of claim 2 wherein said α,β-unsaturated oxo compound is carvone.

5. The process of claim 2 wherein said α,β-unsaturated oxo compound is cyclohex-2-en-1-one.

6. The process of claim 1 wherein said α,β-unsaturated oxo compound is an open-chain compound.

7. The process of claim 6 wherein said open-chain compound is mesityl oxide.

8. The process of claim 6 wherein said open-chain compound is phorone.

9. The process of claim 1 wherein the isomerization catalyst is a monocyclic, aromatic or alicyclic monocarboxylic, dicarboxylic or polycarboxylic acid which may contain a hetero atom and/or be ring-substituted.

10. The process of claim 9, wherein the isomerization catalyst is p-toluic acid, 4-nitro-m-toluic acid or 4-hydroxy-benzoic acid.

11. The process of claim 9, wherein the isomerization catalyst is 3-hydroxy-4-nitrobenzoic acid, 4-trifluoromethylbenzoic acid, vanillic acid, 3,4,5-trimethoxybenzoic acid, 5-nitroisophthalic acid, chelidamic acid or cyclohexane carboxylic acid.

12. The process of claim 1 wherein the isomerization catalyst is an aliphatic or aromatic amino acid.

13. The process of claim 12 wherein the isomerization catalyst is indolebutryic acid or trans-1,2-diaminocyclohexanetetraacetic acid.

14. The process of claim 1 wherein said acid is adipic acid.

15. The process of claim 1 wherein the isomerization catalyst is present in an amount of from about 0.1 to about 20 mole percent, based upon the moles of α,β-unsaturated oxo compound employed as a starting material.

* * * * *